United States Patent [19]

Kramer

[11] 4,357,483
[45] Nov. 2, 1982

[54] AMINOALKYLADAMANTANE CATALYZED ARAFFIN ISOMERIZATION

[75] Inventor: George M. Kramer, Berkeley Heights, N.J.

[73] Assignee: Exxon Research and Engineering Co., Florham Park, N.J.

[21] Appl. No.: 298,117

[22] Filed: Aug. 31, 1981

[51] Int. Cl.³ .............................................. C07C 5/13
[52] U.S. Cl. .................................... 585/740; 585/741; 585/743; 585/745; 585/746; 585/747; 585/749
[58] Field of Search ............... 585/740, 741, 743, 745, 585/746, 747, 749

[56] References Cited

U.S. PATENT DOCUMENTS

| | | | |
|---|---|---|---|
| 2,965,693 | 12/1960 | Kramer | 585/728 |
| 3,231,633 | 1/1966 | Kramer | 585/723 |
| 3,324,196 | 6/1967 | Kramer et al. | 585/725 |
| 3,382,288 | 5/1968 | Schneider | 585/352 |
| 3,546,308 | 12/1970 | Moore | 585/352 |
| 3,551,514 | 12/1970 | Evering | 585/731 |
| 3,671,598 | 6/1972 | Moore | 585/350 |
| 3,689,590 | 9/1972 | Rakow et al. | 585/731 |
| 4,162,233 | 7/1979 | Kramer | 252/429 R |
| 4,229,611 | 10/1980 | Kramer | 585/728 |

OTHER PUBLICATIONS

"Industrial Laboratory Alkylation" edited by Lyle F. Albright and Arthur R. Goldsby, ACS Symposium Series 55, published Washington, D.C., 1977, Chapter One, Alkylation Studies by George M. Kramer.

J. Org. Chem. 44, pp. 2619–2624 (1979) by D. Mirda, D. Rapp and G. M. Kramer.

J. Amer. Chem. Soc. 98, pp. 5864–5870 (1976) by P. Van Pelt and H. M. Buck.

Primary Examiner—Curtis R. Davis
Attorney, Agent, or Firm—Robert J. North

[57] ABSTRACT

A process is described for paraffin isomerization under strong acid conditions in which in aminoalkyladamantane is used to substantially increase the reaction rate of the isomerization.

14 Claims, No Drawings

AMINOALKYLADAMANTANE CATALYZED ARAFFIN ISOMERIZATION

BACKGROUND OF THE INVENTION

This invention relates to a catalytic process for paraffin-isomerization producing branched paraffins under strong acid catalyzed conditions in the presence of aminoalkyladamantanes as hydride transfer catalysts.

Alkylation or isomerization of paraffins under strong acid conditions are well-known processes for producing a wide variety of useful hydrocarbon materials and particularly; gasoline additives. For example, 2,2,4-trimethylpentane is a common blending agent used for gasoline octane improvement which can be produced by alkylating isobutylene with isobutane in sulfuric acid or liquid HF.

An example of an acid-catalyzed reaction process is described in U.S. Pat. No. 3,231,633.

Hydrocarbon conversion processes employing novel Lewis acid systems are disclosed in U.S. Pat. No. 4,229,611 and U.S. Pat. No. 4,162,233, both assigned to Exxon Research and Engineering Company.

U.S. Pat. No. 3,671,598 describes a process for isomerizing saturated cyclic hydrocarbons under strong acid conditions in the presence of an adamantane hydrocarbon. However, no suggestion is made that other specifically substituted adamantanes, particularly those with aminoalkyl substituents, might be more effective in increasing the rate of isomerization of paraffins to branched isomers.

New methods for producing such branched paraffinic hydrocarbons are constantly being searched for in an effort to improve isomerization efficiency. More active catalysts enable these rearrangements to be conducted at lower temperatures where thermodynamic equilibria are more favorable to branched structures, an important factor in butane, pentane and hexane isomerization.

SUMMARY OF THE INVENTION

We have unexpectedly found that the presence of a surface-active aminoalkyladamantane hydrocarbon in a strong acid system containing a paraffinic hydrocarbon rapidly increases the rate of isomerization of said hydrocarbon, presumably through increased intermolecular hydride transfer that the paraffin undergoes in the system. Since intermolecular hydride transfer is generally the rate determining step in paraffin isomerization, (see "Industrial Laboratory Alkylation", edited by Lyle F. Albright and Arthur R. Goldsby, ACS Symposium Series 55, Published Washington, D.C., 1977, Chapter One, "Alkylation Studies" by G. M. Kramer) then the presence of the adamantane hydrocarbon will serve to significantly increase the reaction rate of the isomerization process. In the production of octane-increasing agents, this should lead to the utilization of smaller and more efficient reactors, which enhances the economics of the process.

More specifically, by this invention, there is provided an isomerization process comprising contacting a $C_4$–$C_6$ paraffinic hydrocarbon with a strong acid system and in the presence of an aminoalkyladamantane, containing at least one unsubstituted bridgehead position, at a temperature of about $-100°$ to $150°$ C., thereby producing a branched isomer of said paraffinic hydrocarbon, containing the same number of carbon atoms.

In the process, the total described range of applicable paraffins can be used in the subject isomerization process, under very strong acid conditions, e.g., $AlBr_3$. However, in the slightly weaker acid systems, such as $H_2SO_4$ and HF, n-paraffins like n-butane do not generally undergo the isomerization process and they require the stronger acid systems, as described herein.

DESCRIPTION OF THE INVENTION AND PREFERRED EMBODIMENTS

The reason that an aminoalkyladamantane hydrocarbon serves to increase the rate of intermolecular hydride transfer during branched paraffin isomerization, is not clearly understood. One theory that we do not wish to be bound by is that reversible hydride transfer from the adamantyl group to a carbonium ion in solution is enhanced due to lack of steric repulsions in the transition state involving the adamantyl group when compared to that involving a paraffin.

In the process, $C_4$–$C_6$ paraffinic hydrocarbons are isomerized. As is well-known, the extent of the rearrangement and the possibility of changing the branchiness of the paraffin, as distinct from the possibility of inducing an alkyl shift, depends primarily on the acid system. The aminoalkyladamantane compound catalyzes the process appropriate to the acid employed. Examples of operable paraffins include n-butane, isobutane, isopentane, n-pentane, 2-methylpentane, 3-methylpentane, n-hexane, mixtures thereof, and the like. Preferred paraffins in the process are 2- and 3-methylpentane, n-hexane, n-pentane and n-butane, or refinery streams containing mixtures of these components which are not at their equilibrium concentrations.

The product paraffins in the process are $C_4$–$C_6$ branched paraffinic hydrocarbons. Representative examples include isobutane, isopentane, 2-methylpentane, 3-methylpentane, 2,3-dimethylbutane, 2,2-dimethylbutane, and the like. The preferred product paraffinic hydrocarbons in the process are the most highly branched isomers in each of the $C_4$, $C_5$ and $C_6$ product streams. The product paraffins are useful as gasoline blending agents for octane improvement and/or hydrocarbon solvents.

The phrase "a strong acid system", as used herein, refers to the acid system capable of assisting in generating carbonium ions in the process and includes an "acid component" and a solvent, or one material that can function in both capacities, such as concentrated sulfuric acid or liquid HF. The acid system can be solid, liquid, gaseous or in the vapor phase. Preferably the acid system is a liquid.

The strong acid components in the acid system are conventional protic, aprotic, or Lewis acids and include $AlBr_3$, $AlCl_3$, $GaCl_3$, $TaF_5$, $SbF_5$, $AsF_5$, $BF_3$, HF, HCl, HBr, $H_2SO_4$, $HSO_3F$, $CF_3SO_3H$, and the like and mixtures thereof. A preferred acid component in the process, when aimed at preparing most highly branched products, is $AlBr_3$, $GaCl_3$, or $TaF_5$. If a rapid but limited rearrangement is desired, $H_2SO_4$ or HF would be the preferred acids. An example of the former is the isomerization of n-hexane to dimethylbutanes and an example of the latter is the isomerization of 2-methylpentane to 3-methylpentane. Also, HCl and HBr are preferably not used alone, but are used in combination with other Lewis acids, e.g., $AlCl_3$ or $AlBr_3$.

Also a component of the "acid system", if required, is a solvent for the acid component. For Lewis acids, halogenated paraffins and aromatics are generally used; representative examples include $CH_3Br$, $CH_2Br_2$, CH$_2$Cl$_2$, 1,2-dichloroethane, 1,2,3-trichlorobenzene, 1,2,3,4-tetrachlorobenzene, pentafluorobenzene, HF, H$_2$SO$_4$, CF$_3$SO$_3$H, HSO$_3$F and the like, and mixtures thereof.

The molar concentration of acid component in the solvent, if they are different materials, is generally between 0.1 and 8.0 M, and preferably 0.5 to 4.0 M (moles/liter).

The volume ratio of the acid system to the paraffinic hydrocarbon to be isomerized is generally about 5/1 to 1/5, and preferably about 3/1 to 1/3 parts by volume. However, larger and smaller ratios can be effectively employed.

The aminoalkyladamantane hydrocarbon useful in the process contains at least one aminoalkyl group and at least one unsubstituted bridgehead position, is surface active and can be prepared by conventional methods in the art. By the term "surface active", is meant that the aminoalkyladamantane depresses the surface tension of the acid system when used at low concentration.

The aminoalkyladamantane is preferably of the formula:

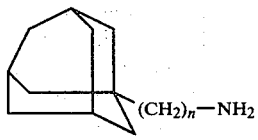

where n=0–10 and wherein the adamantane ring, the alkyl bridge and the amino group can be further modified and substituted with groups which are inert under the process conditions and include C$_1$–C$_4$ alkyl groups for the amine protons and NO$_2$ and CF$_3$ or C$_n$F$_{2n+1}$ (n=1–10) replacements for the remaining protons provided that at least one bridgehead hydrogen remains.

Representative examples include 4-aminobutyl-[1-adamantane], 3-aminopropyl-[1-adamantane], 2-aminoethyl-[1-adamantane], 1-aminomethyl-adamantane, 10-aminodecyl-[1-adamantane], and the corresponding aminoalkyl-2-adamantane derivatives, and the like. Preferred aminoalkyladamantane in the process is 4-aminobutyl-1-adamantane.

The molar concentration of aminoalkyladamantane in the acid solution varies from about 10$^{-6}$ to 10$^{-1}$ moles/liter, and preferably about 10$^{-4}$ to 10$^{-2}$ moles/liter. However, larger and smaller ratios can also be used effectively.

Temperatures in the process are conducted in the range of about −100° to 150° C. and preferably about −50° to 100° C., depending primarily on the temperature required to obtain a liquid-phase catalyst.

The process is normally carried out at atmospheric pressure but may also be conducted at higher pressures up to about 20 atmospheres, the pressure depending primarily on the partial pressure of isobutane in the reaction mixture.

Yields of isomeric hydrocarbons in the process are only limited by the thermodynamic equilibrium at the process temperature, and it is within the scope of this invention to separate undesirable isomers from the mixed product and recycle them for further conversion to the more desirable isomers.

A particularly preferred embodiment of the process is where n-butane is isomerized to isobutane, n-pentane is isomerized to isopentane, and n-hexane is isomerized to a mixture of methylpentanes and dimethylbutanes.

Apparatus for carrying out the subject process is conventional, either in a laboratory, pilot plant, or full industrial scale, and the process can be conducted in a batch-type operation or in a continuous-type operation and in slurry, liquid, gaseous, or vapor phase. Preferred is a continuous-type operation.

Generally, the process is conducted by contacting a liquid mixture of paraffin and aminoalkyladamantane hydrocarbon with the acid system described herein. If the hydrocarbon mixture is miscible with said acid system, then the reaction takes place in a one-phase homogeneous manner. If the acid system is, for example, H$_2$SO$_4$, then the process is conducted in a two-phase manner, the acid system being the lower phase. The entire system is preferably at reaction temperature at time of mixing during which the entire system is adequately mixed, stirred and agitated to insure good contact between the acid system and the hydrocarbon system. The reaction is allowed to progress until a desired or substantial quantity of formed product is obtained. This can be monitored by analytical methods such as gas chromatography and mass spectrometry. After the desired paraffinic product has been formed, the phases can be separated and the hydrocarbon phase treated by extraction of fractional distillation, and the like, to separate out and collect the desired product.

It is to be understood that obvious modifications and variations on the above-described procedure and subject process, not specifically described herein, are deemed to be encompassed within the general scope and spirit of this application.

The following example is illustrative of the best mode of carrying out the invention, as contemplated by me, and should not be construed as being limitations on the scope or spirit of the instant invention.

EXAMPLE

This example shows how a surface active adamantylalkylamine accelerates intermolecular hydride transfer at a sulfuric acid/hydrocarbon interface and results in the faster isomerization of a branched paraffin (3-methylpentane to 2-methylpentane). Table I lists the surface tension of solutions of different molarity, M of 4-aminobutyl-[1-adamantane] in 95.9 percent H$_2$SO$_4$. Also shown are the isomerization rates of 3-methylpentane obtained under well-stirred conditions using equal volumes of hydrocarbon and acid. For comparison, the isomerization rates with no additive and with dodecylamine (a surfactant which cannot function as a hydride transfer intermediate) are also shown.

TABLE I

| Isomerization Of 3-Methylpentane In Conc. H$_2$SO$_4$, 25° C. | | | |
|---|---|---|---|
| Additive, M | Rate Constants, hr. | Rel. Rate | Surface Tension dynes/cm. |
| None | 0.021 | 1.0 | 59.5 |
| AAB[(1)], 0.002 | 0.064 | 3.0 | 59.0 |
| AAB, 0.005 | 0.118 | 5.6 | 57.7 |
| AAB, 0.050 | 0.16 | 7.6 | 50.8 |
| C$_{12}$H$_{25}$NH$_2$, 0.050 | 0.040 | 1.9 | 44.5 |

[(1)]4-aminobutyl-1-adamantane = AAB

The data indicate a sharp increase in the isomerization rate at the concentration at which AAB begins to depress the surface tension of the acid. The comparison between AAB and C$_{12}$H$_{25}$NH$_2$ indicates the value of incorporating hydride transfer capability into the surfactant.

Since the isomerization of 3-methylpentane in $H_2SO_4$ is believed to involve a slow, rate-determining hydride transfer, this example indicates that AAB will catalyze this type of process in conc. $H_2SO_4$.

What is claimed is:

1. An isomerization process comprising contacting a $C_4$–$C_6$ paraffinic hydrocarbon with a strong acid system in the presence of an aminoalkyladamantane containing at least one unsubstituted bridgehead position, at a temperature of about −100° to 150° C., thereby producing a branched isomer of said paraffinic hydrocarbon.

2. The process of claim 1 wherein said paraffinic hydrocarbon is selected from 3-methylpentane, 2-methylpentane, n-hexane, n-pentane, n-butane, isomers thereof, and mixtures thereof.

3. The process of claim 1 wherein said acid system contains an acid component selected from $AlCl_3$, $AlBr_3$, $GaCl_3$, $TaF_5$, $SbF_5$, $AsF_5$, $BF_3$, HF, HBr, HCl, $H_2SO_4$, $HSO_3F$, $CF_3SO_3H$, and mixtures thereof.

4. The process of claim 3 wherein said acid system further contains a solvent selected from $CH_3Br$, $CH_2Br_2$, $CH_2Cl_2$, 1,2-dichloroethane, 1,2,3-trichlorobenzene, 1,2,3,4-tetrachlorobenzene, HF, $H_2SO_4$, $HSO_3F$, $CF_3SO_3H$, and mixtures thereof.

5. The process of claim 1 wherein said aminoalkyladamantane is of the formula:

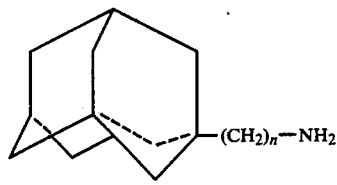

where n=0–10 and the adamantyl ring, alkyl chain, and amino group can be substituted with substituents which are inert or unreactive under the process conditions.

6. The process of claim 1 wherein said adamantane is 4-aminobutyl-[1-adamantane].

7. The process of claim 1 wherein said temperature is in the range of about −50° to 100° C.

8. The process of claim 1 being conducted in a continuous manner.

9. The process of claim 1 wherein said branched paraffin is 3-methylpentane and said product is 2-methylpentane.

10. The process of claim 1 wherein said strong acid system contains $AlCl_3$, $AlBr_3$, $GaCl_3$, or $TaF_5$.

11. The process of claim 10 wherein n-butane is isomerized to isobutane.

12. The process of claim 10 wherein n-pentane is isomerized to isopentane.

13. The process of claim 10 wherein n-hexane is isomerized to a mixture of dimethylbutanes and methylpentanes.

14. The process of claim 10 wherein said paraffin is a mixture of $C_4$, $C_5$ or $C_6$ isomers wherein at least one fraction is not at thermodynamic equilibrium.

* * * * *